(12) United States Patent
Barbaroux et al.

(10) Patent No.: US 9,896,654 B2
(45) Date of Patent: Feb. 20, 2018

(54) SINGLE—USE BIOPHARMACEUTICAL DEVICE FOR PRODUCING, STORING, AND TRANSPORTING A BIOPHARMACEUTICAL MATERIAL, AND CORRESPONDING MULTILAYER TUBE

(75) Inventors: Magali Barbaroux, La Destrousse (FR); Mareva Gueneron, Auriol (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 908 days.

(21) Appl. No.: 13/817,190

(22) PCT Filed: Aug. 10, 2011

(86) PCT No.: PCT/FR2011/051896
§ 371 (c)(1),
(2), (4) Date: Mar. 8, 2013

(87) PCT Pub. No.: WO2012/022906
PCT Pub. Date: Feb. 23, 2012

(65) Prior Publication Data
US 2013/0161229 A1    Jun. 27, 2013

(30) Foreign Application Priority Data
Aug. 17, 2010    (FR) ..................................... 10 56637

(51) Int. Cl.
*C12M 1/00*    (2006.01)
*A61J 1/20*    (2006.01)
(Continued)

(52) U.S. Cl.
CPC ................ *C12M 23/20* (2013.01); *A61J 1/20* (2013.01); *B32B 1/08* (2013.01); *B32B 27/08* (2013.01);
(Continued)

(58) Field of Classification Search
CPC ...... C12M 23/20; B32B 27/00; B32B 27/304; B32B 27/306; B32B 27/32; B32B 27/322; B32B 439/80; A61B 10/0096
(Continued)

(56) References Cited

U.S. PATENT DOCUMENTS 4,707,389 A    11/1987    Ward
5,356,709 A *  10/1994    Woo ...................... A61L 29/049
                                                      156/294
(Continued)

FOREIGN PATENT DOCUMENTS

EP    0203265    * 11/1982
EP    0 136 848    4/1985
(Continued)

OTHER PUBLICATIONS

International Search Report dated Oct. 26, 2011, corresponding to PCT/FR2011/051896.

*Primary Examiner* — William H Beisner
(74) *Attorney, Agent, or Firm* — Young & Thompson

(57) ABSTRACT

A device including: a bag, a tube section having a wall defining a free longitudinal space, and a plastic connector, which are all fused together, the wall including a contact layer made of a material other than PVC, selected from PE, EVA, PP, ETFE, and PVDF, and a functional layer including at least one basic functional layer of a material selected for the function thereof (flexibility, sturdiness, handling, opacity or transparence, gas barrier) and selected from the family including PE, PET, a PA, EVA, EVOH, SEBS, PETG, and PVDF, a bag, another tube section, and/or a connector fused to the biopharmaceutical tube and including a contact layer made of a material capable of being in contact with the biopharmaceutical material, which is capable of being fused (Continued)

onto itself, and which is identical or similar to the material of the contact layer of the biopharmaceutical tube.

14 Claims, 6 Drawing Sheets

(51) Int. Cl.

| | |
|---|---|
| *B32B 27/30* | (2006.01) |
| *B32B 27/32* | (2006.01) |
| *B32B 27/08* | (2006.01) |
| *B32B 27/34* | (2006.01) |
| *B32B 27/36* | (2006.01) |
| *B32B 1/08* | (2006.01) |
| *A61B 10/00* | (2006.01) |
| *F16L 11/04* | (2006.01) |

(52) U.S. Cl.
CPC .......... *B32B 27/302* (2013.01); *B32B 27/304* (2013.01); *B32B 27/306* (2013.01); *B32B 27/32* (2013.01); *B32B 27/322* (2013.01); *B32B 27/34* (2013.01); *B32B 27/36* (2013.01); *A61B 10/0096* (2013.01); *B32B 2307/41* (2013.01); *B32B 2307/412* (2013.01); *B32B 2307/536* (2013.01); *B32B 2307/546* (2013.01); *B32B 2307/7163* (2013.01); *B32B 2307/72* (2013.01); *B32B 2307/7242* (2013.01); *B32B 2439/80* (2013.01); *B32B 2535/00* (2013.01); *B32B 2597/00* (2013.01); *F16L 11/045* (2013.01)

(58) Field of Classification Search
USPC ....................................................... 435/289.1
See application file for complete search history.

(56) References Cited

U.S. PATENT DOCUMENTS

| | | | |
|---|---|---|---|
| 5,562,127 A | 10/1996 | Fanselow et al. | |
| 5,928,744 A | 7/1999 | Heilmann et al. | |
| 5,988,422 A * | 11/1999 | Vallot ........................ | 220/62.22 |
| 6,187,400 B1 | 2/2001 | Woo et al. | |
| 2002/0132077 A1* | 9/2002 | Ling ........................ | B32B 1/08 |
| | | | 428/36.91 |
| 2002/0147440 A1* | 10/2002 | Samolyk ................... | A61J 1/10 |
| | | | 604/411 |
| 2006/0264898 A1* | 11/2006 | Beasley et al. ............... | 604/506 |
| 2009/0299260 A1 | 12/2009 | Kreischer et al. | |
| 2010/0137838 A1 | 6/2010 | Hwang | |

FOREIGN PATENT DOCUMENTS

| | | |
|---|---|---|
| EP | 0 712 354 | 5/1996 |
| EP | 0765740 | 9/1997 |
| EP | 0999860 | 5/2000 |
| WO | 95/04652 | 2/1995 |
| WO | 99/61083 | 12/1999 |
| WO | 00/04131 | 1/2000 |
| WO | 00/13896 | 3/2000 |
| WO | 2010051468 | 5/2010 |

* cited by examiner

SINGLE—USE BIOPHARMACEUTICAL DEVICE FOR PRODUCING, STORING, AND TRANSPORTING A BIOPHARMACEUTICAL MATERIAL, AND CORRESPONDING MULTILAYER TUBE

BACKGROUND OF THE INVENTION

Field of the Invention

A singe-use biopharmaceutical device for producing, storing, and transporting a biopharmaceutical substance, and a corresponding multilayer tube The invention relates to biopharmaceutical tubes specially adapted and designed for single-use biopharmaceutical devices for producing, storing, and transporting biopharmaceutical substances.

It relates more especially to a single-use biopharmaceutical device for producing, storing, and transporting biopharmaceutical substance, said device comprising at least one segment of multilayer biopharmaceutical tube, a multilayer tube specially adapted and designed for such a device, and a method of manufacturing such a biopharmaceutical device.

DESCRIPTION OF THE RELATED ART

The term "biopharmaceutical substance" is used herein to mean a substance produced by biotechnology—culture medium, cell culture, buffer solution, etc.—or a pharmaceutical substance.

Biopharmaceutical devices are known that are designed to produce, store, and transport such a biopharmaceutical substance, such devices being of the type comprising at least one—and possibly more—pharmaceutical receptacle(s) having one—and usually more—inlet or outlet access(es) (or port(s)) and at least one—and usually more—segments of biopharmaceutical tubes arranged in such a manner that an end portion of a segment of tube is—or can be—associated in communicating, continuous, rigid, and leaktight manner, and directly or indirectly, with an access of a receptacle, e.g. via a biopharmaceutical connector. Such a biopharmaceutical device is also generally associated with one—and usually—more flow-stop devices for stopping the biopharmaceutical substance from flowing. Finally, such a biopharmaceutical device may, optionally, be associated with one or more biopharmaceutical systems for mixing or aeration, which systems may be said to be "functional biopharmaceutical systems". Non-limiting examples of such biopharmaceutical devices are mixing devices and bioreactors.

The term "tube" is used herein to mean a hollow vessel, elongate and of a certain finite length, of generally cylindrical shape or of generally pseudo-cylindrical shape, open at one end or at both ends, and suitable for being filled with a certain fluid content for moving said fluid content or for allowing it to stand. Such a tube comprises a peripheral sidewall and a longitudinal empty space, and optionally a plurality of longitudinal empty spaces, separated by one or more walls. The term "tube" may herein be considered to be synonymous with "duct", "conduit", or "pipe". It is understood that the tube in question is especially suitable for use in a biopharmaceutical device for producing, storing, and transporting a biopharmaceutical substance, as described above, which excludes a catheter or an analogous device or a tube for extracorporeal circulation of blood or for passing fluid during a dialysis, a perfusion, or artificial feeding, or for an analogous purpose and an analogous application, lying within some other technical field.

By synecdoche, the term "tube" applies both when the tube is of long length, as results from its manufacturing process, and also when the tube is of smaller length, such as when it has the length of a segment resulting from cutting a long length and designed to be incorporated into the biopharmaceutical device for preparing, storing and transporting a biopharmaceutical substance.

Conventionally, the receptacles and the tubes of such production, storage, and transport biopharmaceutical devices were originally rigid and made of stainless steel, so as to enable them to be implemented recurrently. As taught by the article entitled *Stainless Steel Tubing in the Biotechnology Industry* published in *Pharmaceutical Engineering* 2001, vol. 21, No. 5, pages 48-63, stainless is well qualified not only because it has a long life, but also for its availability, its machinability or "fabricability", its properties of being non-corrosive, of being non-contaminant, of being suitable for being polished to a smooth finish, of being strong and rigid, of being capable of withstanding heat and chemical sterilization treatments, and of being easy to weld. With such a biopharmaceutical device, it is possible to consider associating a tube directly with a receptacle or with another tube, by welding. In addition, a flow-stop device for stopping the biopharmaceutical substance from flowing is typically in the form of a valve.

Then, such biopharmaceutical devices were designed to be single-use devices, having a certain amount of flexibility and, to that end, made of plastic. In particular, such a device offers the advantages of being easier to fit or install, of reducing idle time, of optimizing the use of the floor area, and of very significantly reducing the risk of cross-contamination.

Such a biopharmaceutical device comprises at least one—and optionally more—bag(s), at least one—and optionally more—segment(s) of tube and at least one—and optionally more—biopharmaceutical connectors. These component elements, each of which is a single-use element, are mutually associated in communicating, continuous, rigid, and leaktight manner. They have a certain amount of flexibility and are made of plastic. With such a biopharmaceutical device, a tube is associated with a receptacle proper via a biopharmaceutical connector. A flow-stop device for stopping the biopharmaceutical substance from flowing is then typically in the form of a clamp that comes to close the flexible portion of the pharmaceutical device at the place in which it is located, by flattening said portion.

Regarding such a biopharmaceutical device, a biopharmaceutical bag is known that has its two large walls fused or otherwise bonded together (i.e. a two-dimensional (2D) bag). For example Document EP-A-0 136 848 relates to such a bag. A 3D bag is also known that has two end walls and one side wall that can be folded flat or unfolded and deployed, the walls being fused together, and it being possible for the volume to reach 3000 liters, or even more. For example, such a 3D bag is described in Document W000/04131 and is sold by Sartorius under the trademark FLEXEL® 3D.

The walls of such biopharmaceutical bags are essentially continuous overall and they have an outside face in contact with the outside environment of the bag and an inside face with which the pharmaceutical substance filling the bag is in contact. The material of which the inside face is made can, for example, be chosen from the family comprising polyethylene (PE) and in particular linear low-density polyethylene (LLDPE), polyethylene vinyl acetate (EVA), polypropylene (PP), ethylene-tetrafluoroethylene (ETFE), polyvinylidene fluoride (PVDF), and equivalent materials, in the context of the purpose and application in question.

The walls of such biopharmaceutical bags are chosen, in particular as regards their component materials, their shapes, their dimensions, etc., so as to be suitable firstly for having a property of containing the contents of the bag and of physically separating said contents from the outside of the bag, and, secondly, of having physical, chemical, biological, and operational properties adapted to the purpose and application in question. Merely by way of non-limiting example, such physical, chemical, biological, and operational properties may be: providing a barrier having a high degree of impermeability to gas; being capable of mechanically containing the biopharmaceutical substance that is in the bag, the volume of which may vary to various degrees; being capable of avoiding undesirable interactions with the environment or with the biopharmaceutical substance; being clean, in particular with regard to particles or biologically; being non-degradable, and having high chemical resistance; enabling the biopharmaceutical substance to be produced, stored, transported, and used safely; being suitable for being fused or otherwise bonded; being easily folded and unfolded without being damaged; and having qualities as regards, in particular, adherence, flexibility, opacity or, conversely, transparence, these characteristics being in no way exclusive of other characteristics.

Initially, conventional tubes made of silicone or of polyvinyl chloride (PVC) were used for tubes in such single-use biopharmaceutical devices for producing, storing, and transporting biopharmaceutical substances.

However, Documents EP-A-0 712 354, EP-A-0 999 860, US 2009/0299260, WO 2010/051468 and WO 95/04652 teach that, alongside numerous advantages (such as, in particular, flexibility, transparence, capacity to withstand clamping by a clamp without being damaged, and cost), PVC also suffers from drawbacks as regards being used in single-use biopharmaceutical devices, e.g. its dangerousness as regards it being recycled and incinerated, and its temperature-related degradation). Single-layer tubes were therefore made of other materials such as LLDPE or linear high-density polyethylene (LHDPE), EVA, or polybutylene.

Document WO 95/04652 describes a multilayer tube that has at least one inner layer of at least one chlorine-free thermoplastic polymer having flexibility similar to or greater than the flexibility of medical tubes made of PVC, and at least one outer surface layer of at least one second chlorine-free thermoplastic polymer that is tough and that has a Young's modulus not exceeding about fifteen times the Young's modulus of the first thermoplastic polymer.

Document EP-A-0 999 860 teaches that the use of polyolefins or of compounds based on polyolefins makes it possible to overcome the drawbacks of PVC but is a source of other drawbacks such as that of destroying the tube when said tube is clamped with a clamp.

The state of the art teaches various versions (i.e. compositions) of multilayer tubes that are especially adapted to being incorporated into single-use production, storage, and transport biopharmaceutical devices of the type exposed above.

Thus, Document EP-A-0 712 354 describes a multilayer tube comprising an inner layer of at least one first chlorine-free thermoplastic having a chosen flexibility and an outer surface layer of at least one second chlorine-free thermoplastic polymer having flexibility chosen to be greater than the flexibility of the first thermoplastic polymer.

Document EP-A-0 136 848 describes a co-extruded multilayer access tube comprising an outer layer of EVA, an inner layer of PVC, and a bonding layer between them. The end of a membrane tube that is also made of PVC is engaged into one end of such a tube, sufficiently rigid bonding being provided between them by means of bonding based on cyclohexanone.

Document US 2010/0137838 describes a multilayer access tube having a co-extruded medical bag and made up of three layers, namely an inner first layer comprising 50% to 90% by weight of PP-based elastomer and 10% to 50% by weight of PP, an intermediate layer comprising in the range 45% by weight to 55% by weight of PP-based elastomer and 45% to 55% by weight of PP, and an outer layer comprising 20% to 55% by weight of PP-based elastomer and 45% to 80% by weight of PP.

In the different field of medical-use multilayer tubes, Document US 2009/0299260 describes a multilayer tube not including PVC, and comprising three layers of materials chosen from the family comprising PE, PP, and copolymers thereof, terpolymers thereof, and mixtures thereof, the intermediate layer including at least 60% of thermoplastic elastomer. Provision is made for two of such tubes to be associated by means of a polyolefin connector by laser welds. In that document, such a multilayer tube is specially designed for extracorporeal circulation of blood, and is thus specially arranged to be suitable for being associated with a peristaltic pump. Conversely, such a multilayer tube is not designed to be incorporated into a biopharmaceutical device as defined above.

Similarly, Document EP-A-0 765 740 describes a multilayer tube that is PVC-free and that comprises at least two layers, namely an inner or an outer first layer formed mainly of isoprene-based synthetic rubber or of PP and, in particular, having density and Shore hardness that are chosen so that it is suitable for being heat-sterilized at a temperature of 121° C., and an outer or an inner second layer formed mainly of a chosen PE copolymer or of a chosen synthetic rubber. In that document, such a multilayer tube is specially designed for passing fluid during dialysis, perfusion, or artificial feeding. As above, it is not designed to be incorporated into a biopharmaceutical device as defined above.

Also, Document WO 99/61083 describes a pump tube having one or more layers, and for medical use, but not incorporated into a biopharmaceutical device as defined above.

Document WO 00/13896 describes multilayer structures comprising at least one layer made of an ethylene/alpha-olefin having a density of less than 0.916 grams per cubic centimeter (g/cc) and a maximum melting point greater than 118° C. Such a multilayer structure has at least three layers. Such multilayer structures make it possible to produce manufactured articles, in particular films, receptacles, bags, packaging, tubes, and the like.

Therefore, like the need for biopharmaceutical bags for single-use production, storage, and transport biopharmaceutical devices, there exists the need to have biopharmaceutical tubes specially designed for such biopharmaceutical devices and that have a certain amount of flexibility, that are made of plastic, and that, in particular due to their component materials, are suitable firstly for having a property of containing the contents of the tube and of physically separating said contents from the outside of the tube, and, secondly, of having physical, chemical, biological, and operational properties adapted to the purpose and application in question. Merely by way of non-limiting example, such physical, chemical, biological, and operational properties may be:

providing a barrier having a high degree of impermeability to gas; being capable of being filled with the biopharmaceutical substance; being capable of avoiding undesirable interactions with the environment or with the biopharmaceutical substance; being clean, in particular with regard to particles or biologically; being non-degradable, and having high chemical resistance; enabling the biopharmaceutical substance to be produced, stored, transported, and used safely; being suitable for being fused; being easily bendable without being damaged; and having qualities as regards, in particular, adherence, opacity or, conversely, transparence, and flexibility, to the extent of being closable by being flattened by means of a clamp, these characteristics being in no way exclusive of other characteristics.

In addition, there is a need to have such biopharmaceutical tubes that are specially designed for such biopharmaceutical devices that are adapted to the increasingly demanding flexibility and versatility constraints, in particular depending on the biopharmaceutical substance in question, on the nature and on the characteristics of the single-use production, storage, and transport biopharmaceutical device implemented and on the uses made of such devices. At the same time, it is necessary for users always to have guarantees as regards the component materials of such tubes and more especially as regards the material of the inside face of the tube that is in contact with the biopharmaceutical substance.

There also exists a need for the biopharmaceutical tube(s) of such a single-use biopharmaceutical device to be able to be associated in communicating, continuous, rigid, and leaktight manner with the biopharmaceutical bag(s) of the device, optionally via one—or more—biopharmaceutical connectors, optionally, for connecting to one—or more—other biopharmaceutical tubes. And it is desirable for the material of the inside faces of all of the component elements of the single-use biopharmaceutical device that are in contact with the biopharmaceutical substance to be the same and for there to be full physical continuity, or at least as much physical continuity as possible, between the various successive inside faces of the various component elements of the biopharmaceutical device.

SUMMARY OF THE INVENTION

The problem to be solved by the invention is to meet all of these needs and requirements.

In a first aspect, the solution to this problem is provided by a single-use biopharmaceutical device for producing, storing, and transporting biopharmaceutical substance, said device comprising: at least one multilayer segment of biopharmaceutical tube, having a peripheral side wall delimiting a longitudinal empty space and including a contact layer and a functional layer with the outer face of the contact layer and the inner face of the functional layer being secured together; at least one biopharmaceutical bag; and, optionally, at least one biopharmaceutical connector; each of these component elements being single-use and having a contact layer made of a material chosen to be suitable for being in contact with the biopharmaceutical product without resulting in degradation of the contact layer or of the biopharmaceutical substance, and for being weldable to itself, these elements being welded together in communicating, continuous, rigid, and leaktight manner, having a certain amount of flexibility, and being made of plastic.

Such a biopharmaceutical device is such that:
the contact layer of the biopharmaceutical tube is made of a material chosen to be suitable for being in contact with the biopharmaceutical substance without resulting in degradation of the contact layer and of the biopharmaceutical substance and for being weldable to itself, other than PVC, and chosen from the family comprising polyethylene (PE) and in particular linear low-density polyethylene (LLDPE), polyethylene vinyl acetate (EVA), polypropylene (PP), ethylene-tetrafluoroethylene (ETFE), and polyvinylidene fluoride (PVDF), the inside face limiting the longitudinal empty space and being suitable for being in contact with the biopharmaceutical substance, i.e. being suitable essentially for performing the containing and physical separation function of the at least one biopharmaceutical tube and forming said inside face thereof;

the functional layer of the biopharmaceutical tube includes at least one functional elementary layer made of a material chosen for its flexibility, robustness, handling, opacity or, conversely, transparence, capacity for providing a barrier to gases non-degradable intrinsically or in association with a protective layer, other than PVC and chosen from the family comprising polyethylene (PE) and in particular linear low-density polyethylene (LLDPE), polyethylene terephthalate (PET), a polyamide (PA), polyethylene vinyl acetate (EVA), ethylene vinyl alcohol (EVOH), styrene ethylene butadiene styrene (SEBS), polyethylene terephthalate glycol (PETG), and polyvinylidene fluoride (PVDF), i.e. suitable for performing the functions making it possible to satisfy the other physical, chemical, biological, and operational properties adapted to the relevant purpose and application of the single-use biopharmaceutical device;

the contact layer of the bag, of another segment of tube and/or of a connector, is made of a material chosen to be identical or analogous to the material of the contact layer of the at least one biopharmaceutical tube, the contact layer of the biopharmaceutical tube is welded to the contact layer of the bag, of another segment of tube and/or of a connector, with substantial physical continuity between the respective contact layers.

In an embodiment, a biopharmaceutical bag, and optionally another segment of biopharmaceutical tube and/or a biopharmaceutical connector, welded to at least one biopharmaceutical tube, has/have a multilayer structure that is identical or analogous to the multilayer structure of the at least one multilayer biopharmaceutical tube, namely comprising a contact layer and a functional layer including at least one functional elementary layer. In particular, the functional layer of the at least one biopharmaceutical tube is welded to the functional layer of the biopharmaceutical bag, and optionally of the other segment of biopharmaceutical tube and/or of the biopharmaceutical connector.

Depending on the embodiments, the at least one biopharmaceutical tube is fused to the other component element of the biopharmaceutical bag (1) either directly, thereby intrinsically forming the biopharmaceutical connector, or indirectly via a biopharmaceutical connector.

In an embodiment, the single-use biopharmaceutical device for producing, storing, and transporting biopharmaceutical substance is associated structurally and functionally, removably or non-removably, with at least one flow-stop device for stopping the biopharmaceutical substance from flowing in the longitudinal empty space of the at least one biopharmaceutical tube, having the form of a clamp suitable for closing the portion of the at least one biopharmaceutical tube at which it is located by flattening the at least one biopharmaceutical tube on itself.

Depending on the embodiments, the single-use biopharmaceutical device for producing, storing, and transporting biopharmaceutical substance constitutes a bag for storing and/or filling and/or handling and/or transporting and/or mixing a biopharmaceutical substance or a bioreactor of a biopharmaceutical substance.

In a second aspect, the invention provides a multilayer biopharmaceutical tube having a peripheral side wall limiting a longitudinal empty space, having a certain amount of flexibility and made of plastic, and including a contact layer and a functional layer with the outer face of the contact layer and the inner face of the functional layer being secured together.

This tube is such that:
the contact layer is made of a material chosen to be suitable for being in contact with the biopharmaceutical substance without resulting in degradation of the contact layer and of the biopharmaceutical substance and for being welded on itself, other than PVC, and chosen from the family comprising polyethylene (PE) and in particular linear low-density polyethylene (LLDPE), polyethylene vinyl acetate (EVA), polypropylene (PP), ethylene-tetrafluoroethylene (ETFE), and polyvinylidene fluoride (PVDF), the inside face of the contact layer limiting the longitudinal empty space and being suitable for being in contact with the biopharmaceutical substance, i.e. suitable essentially for performing the containing and physical separation function of the at least one biopharmaceutical tube and forming the inside face thereof;
the functional layer includes at least one functional elementary layer made of a material chosen for its flexibility, robustness, handling, opacity or, conversely, transparence, barrier to gases, non-degradable intrinsically or in association with a protective layer, other than PVC and chosen from the family comprising polyethylene (PE) and in particular linear low-density polyethylene (LLDPE), polyethylene terephthalate (PET), a polyamide (PA), polyethylene vinyl acetate (EVA), ethylene vinyl alcohol (EVOH), styrene ethylene butadiene styrene (SEBS), polyethylene terephthalate glycol (PETG), and polyvinylidene fluoride (PVDF), i.e. suitable for performing the functions making it possible to satisfy the other physical, chemical, biological, and operational properties adapted to the relevant purpose and application of the single-use biopharmaceutical device.

In addition, this biopharmaceutical tube is such that it is specially designed for a single-use biopharmaceutical device for producing, storing, and transporting biopharmaceutical substance, the contact layer of the biopharmaceutical tube being suitable and designed for being welded to the contact layer of the bag, of another segment of tube and/or of a connector of the single-use biopharmaceutical device of a material chosen to be identical or analogous to the material of the contact layer of the biopharmaceutical tube, substantially with substantial physical continuity between the respective contact layers of the tube and of the bag.

In an embodiment, the multilayer biopharmaceutical tube is made up of the contact layer and of the functional layer, the functional layer forming the outside face of the multilayer biopharmaceutical tube.

In a first embodiment, the multilayer biopharmaceutical tube comprises a single functional elementary layer. In a second embodiment, it comprises a plurality of functional elementary layers, each of secured to the or to adjacent layer.

In an embodiment, the outer face of the contact layer and the inner face of the functional layer are secured together by manufacturing, by co-extrusion or embedding or cladding.

In a particular variant of the first embodiment: associated with a contact layer of LLDPE, the multilayer biopharmaceutical tube includes a functional elementary layer of PE.

In a particular variant of the second embodiment: associated with a contact layer of LLDPE, the multilayer biopharmaceutical tube includes a functional elementary layer of EVOH, a functional elementary layer of PA, and a functional elementary layer of PET that forms the outside face of the multilayer biopharmaceutical tube.

In another particular variant of the second embodiment: associated with a contact layer of LLDPE, the multilayer biopharmaceutical tube includes a functional elementary layer of EVOH, a functional elementary layer of PA, two functional elementary layers of LLDPE, and a functional elementary layer of a biodegradable material that forms the outside face of the multilayer biopharmaceutical tube.

In another particular variant of the second embodiment: associated with a contact layer of LLDPE, the multilayer biopharmaceutical tube includes a functional elementary layer of a biodegradable material, two functional elementary layers of LLDPE, a functional elementary layer of EVOH, and a functional elementary layer of PA that forms the outside face of the multilayer biopharmaceutical tube.

In another particular variant of the second embodiment: associated with a contact layer of PE, the multilayer biopharmaceutical tube includes a functional elementary layer of EVA, a functional elementary layer of EVOH, a functional elementary layer of EVA, and a functional elementary layer of PE that forms the outside face of the multilayer biopharmaceutical tube.

In a particular variant of the second embodiment: associated with a contact layer of LLDPE, the multilayer biopharmaceutical tube includes a functional elementary layer of EVOH, a functional elementary layer of LLDPE, and a functional elementary layer of PE that forms the outside face of the multilayer biopharmaceutical tube.

In an embodiment, the multilayer biopharmaceutical tube is circular or oblong cross-section.

Depending on the embodiments, the multilayer biopharmaceutical tube includes a single longitudinal empty space or a plurality of longitudinal empty spaces juxtaposed with leaktight separation.

Depending on the embodiments, the multilayer biopharmaceutical tube is homogeneous from one end to the other of the segment that it forms or, conversely, at least one end of the segment that it forms, it has an uncovered projecting portion constituted by the contact layer, such a segment of multilayer biopharmaceutical tube also performing the function of connector for the single-use biopharmaceutical device for producing, storing, and transporting biopharmaceutical substance.

In a third aspect, the invention provides a method of manufacturing a single-use biopharmaceutical device for producing, storing, and transporting biopharmaceutical substance as described above, disposed of at least one biopharmaceutical bag, at least one segment of biopharmaceutical tube, and, optionally, at least one biopharmaceutical connector, and in positioning these elements in the configuration of the biopharmaceutical device to be manufactured, and in welding them together in communicating, continuous, rigid, and leaktight manner, so that the contact layer of the at least one biopharmaceutical tube is be welded to the contact layer of the biopharmaceutical bag, of another segment of biopharmaceutical tube or, optionally, of the biopharmaceutical connector, with substantial physical continuity between the respective contact layers.

BRIEF DESCRIPTION OF THE DRAWING FIGURES

Embodiments of the invention are described below with reference to the drawings, in which:

FIG. 1 is a perspective view of a possible embodiment given by way of example of a single-use biopharmaceutical device of the invention for producing, storing, and transporting a biopharmaceutical substance, said device comprising, in this example, a biopharmaceutical bag, a biopharmaceutical connector, and a segment of biopharmaceutical tube, each of which is a single-use element, and all of which are fused together in communicating, continuous, rigid, and leaktight manner, have certain amounts of flexibility, and are made of plastic.

Figure 4A:
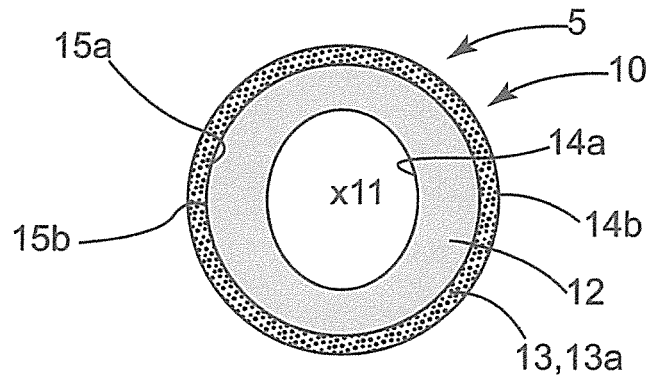
Figure 4B:
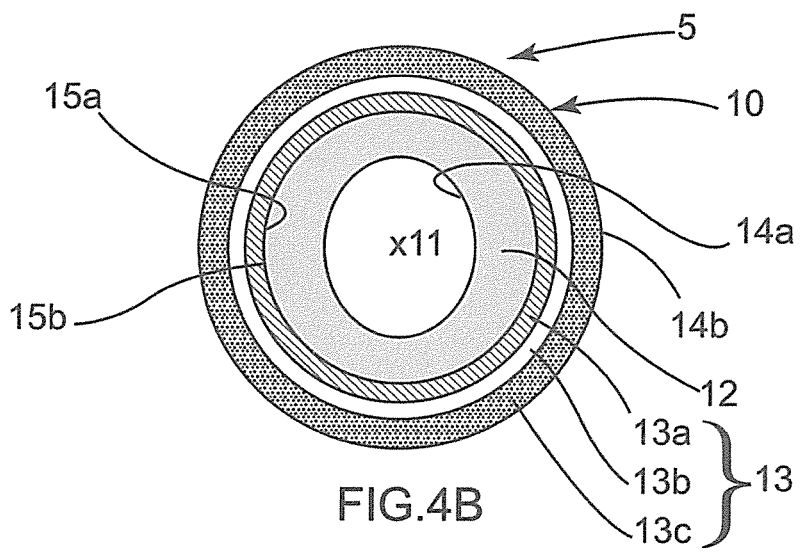
Figure 4C:
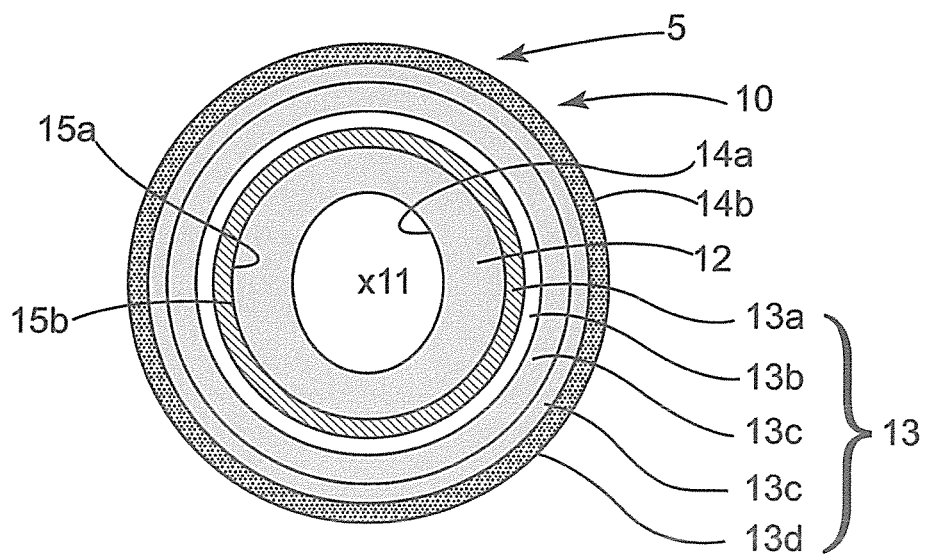
Figure 4D:
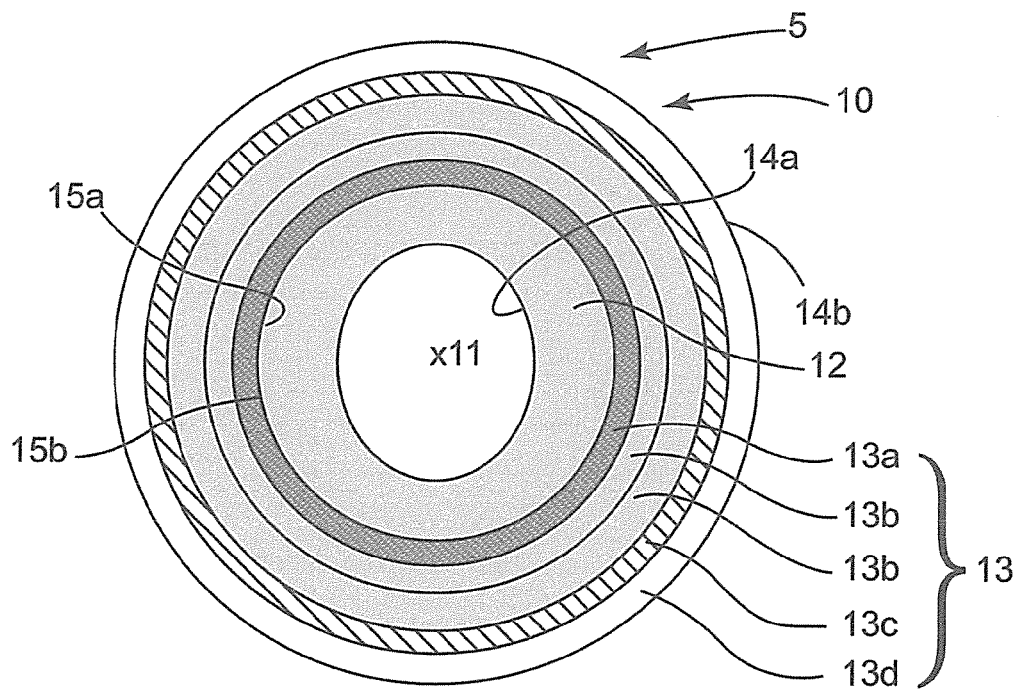
Figure 4E:
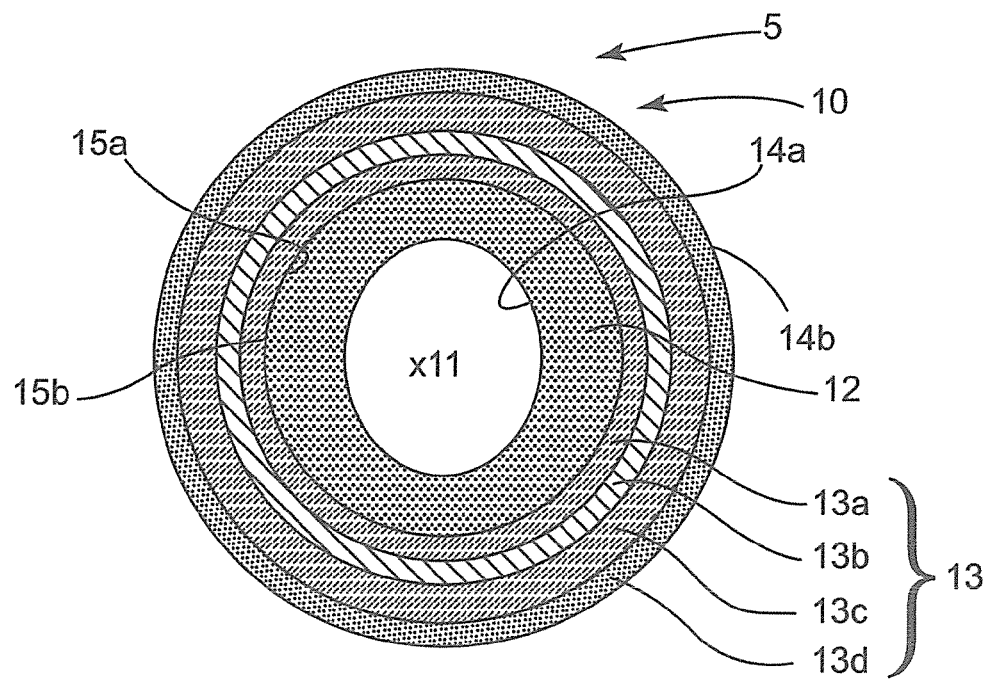
Figure 4F:
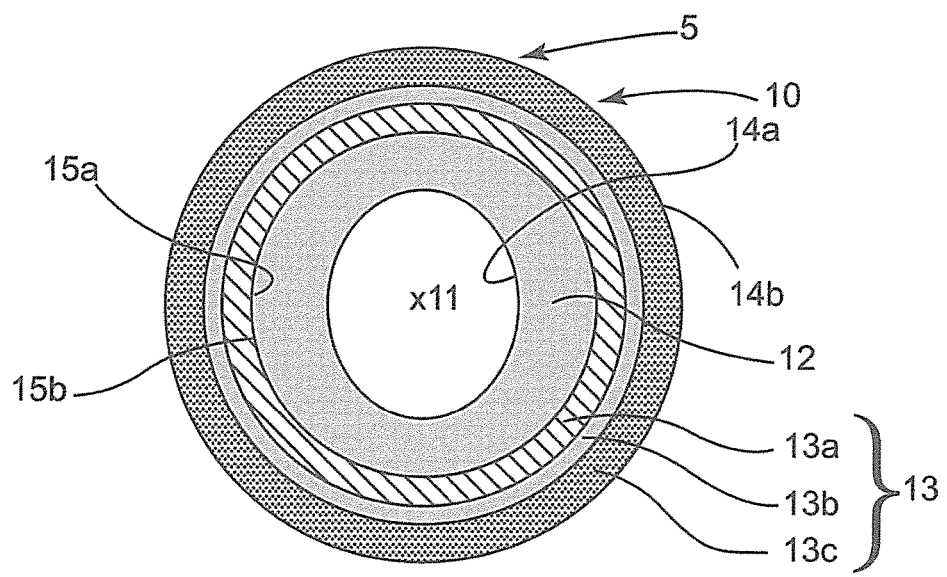

FIGS. 4A, 4B, 4C, 4D, 4E, and 4F are six fragmentary views in cross-section showing various embodiments of multilayer biopharmaceutical tubes, namely a tube including a contact layer of LLDPE and a single functional elementary layer of PE (FIG. 4A), a tube including a contact layer of LLDPE and functional elementary layers of EVOH, of PA, and of PET (FIG. 4B), a tube including a contact layer of LLDPE, and functional elementary layers of EVOH, of PA, of LLDPE, and of a biodegradable material (FIG. 4C), a tube including a contact layer of LLDPE and functional elementary layers of biodegradable material, of LLDPE, of EVOH, and of PA (FIG. 4D), a tube including a contact layer of PE and functional elementary layers of EVA, of EVOH, of EVA, and of PE (FIG. 4E), and a tube including a contact layer of LLDPE and functional elementary layers of EVOH, of LLDPE, and of PE (FIG. 4F).

DETAILED DESCRIPTION OF THE INVENTION

Figure 1:
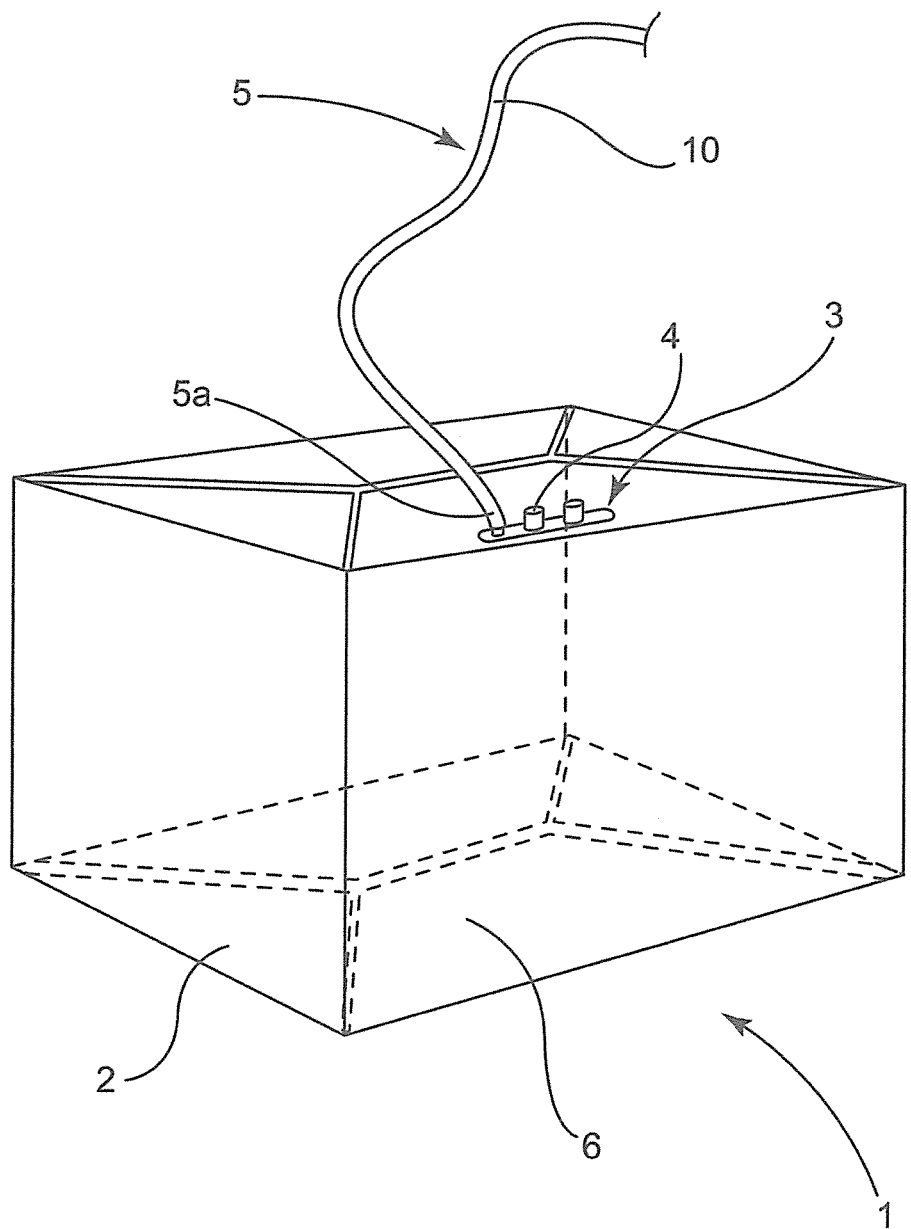
Figure 2:
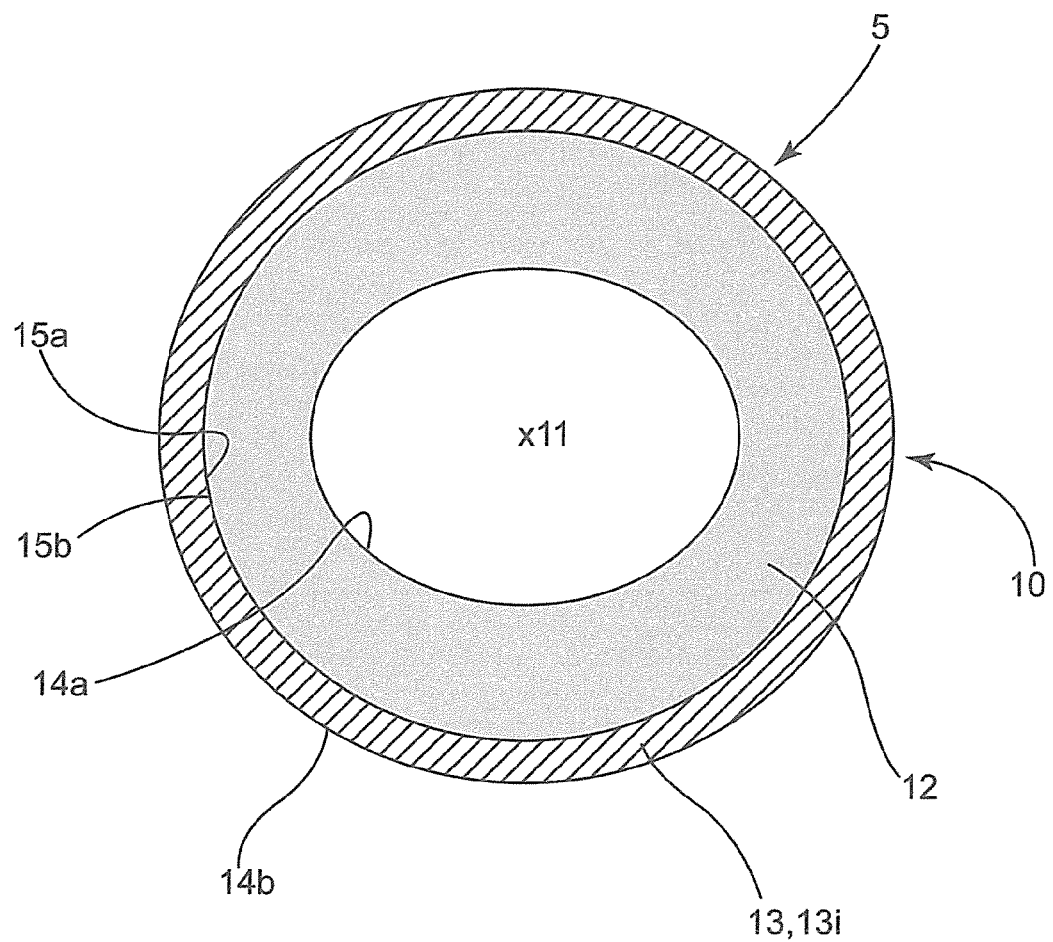
FIG. 2 is a cross-section view of the segment of multilayer biopharmaceutical tube that is part of the single-use biopharmaceutical device of FIG. 1, in a possible embodiment given by way of example in which the tube includes a contact layer and a functional elementary layer.
Figure 3:
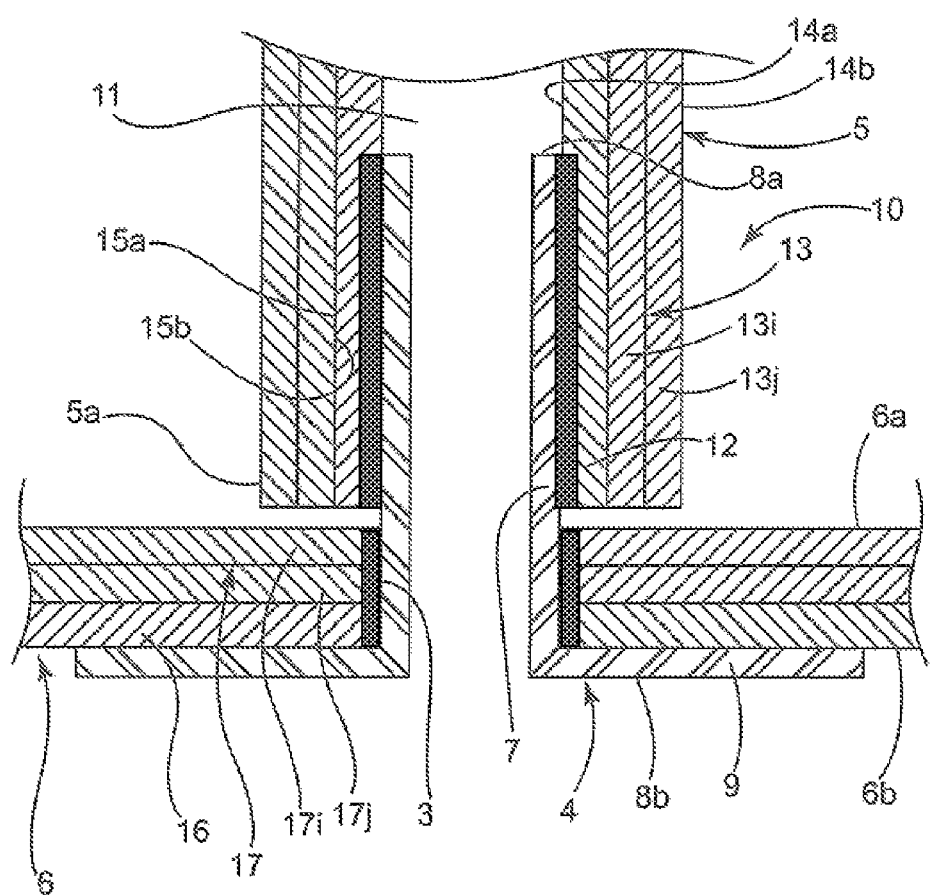
FIG. 3 is a fragmentary view in longitudinal section showing the communicating, continuous, rigid, and leaktight association of the biopharmaceutical bag, of the biopharmaceutical connector, and of the segment of biopharmaceutical tube of FIG. 1.

FIG. 1 shows, merely by way of non-limiting example, a single-use biopharmaceutical device 1 designed for producing, storing, and transporting a biopharmaceutical substance.

The term "biopharmaceutical substance" is used to mean a substance produced by biotechnology—culture medium, cell culture, buffer solution, etc.—or a pharmaceutical substance.

The biopharmaceutical device 1 that is shown comprises: a biopharmaceutical receptacle, which, in this example, is a bag 2 that is three-dimensional (a 3D bag), that has inlet or outlet accesses (or ports) 3; a hollow biopharmaceutical connector 4; and a segment of biopharmaceutical tube 5 having an end portion 5a at one of its ends. Each of these component elements 2, 4, 5 of the biopharmaceutical device 1 is a single-use device and is made of plastic so as to have a certain amount of flexibility (especially for the bag 2 and for the segment of tube 5, it being possible, optionally, for the connector 4 to be more rigid). In the assembled biopharmaceutical device 1, these component elements 2, 4, 5 are associated with one another functionally and structurally by being fused together in communicating, continuous, rigid, and leaktight manner in the arrangement that corresponds to the purpose and application in question. Optionally, in the assembled biopharmaceutical device 1, a segment of biopharmaceutical tube 5 may be associated functionally to some other segment of biopharmaceutical tube 5, the characteristics of which are identical or analogous to the characteristics of this biopharmaceutical tube.

In another embodiment given merely by way of non-limiting example, the segment of biopharmaceutical tube 5 itself forms a biopharmaceutical connector, being associated directly with the biopharmaceutical bag 2, its end portion being provided with a transverse flange, extending outwards, analogous to the transverse flange 9 of a biopharmaceutical connector 4 described below.

For example, a 3D bag 2 is described in Document WO00/04131. The bag 2 of the biopharmaceutical device 1 may also be of the 2D type, with two large walls fused together.

The peripheral side walls 6 of such biopharmaceutical bags 2 are essentially continuous overall and they have an outside face 6a in contact with the outside environment of the bag 2 and an inside face 6b with which the pharmaceutical substance filling the bag is in contact.

The term "outside" relates to what is outside or on the outside of the device 1 or of the component element in question (in particular, the ambient environment in which it finds itself), the term "inside" relates to what is inside or on the inside of the device 1 or of the component element in question (in particular what is in contact with or is suitable for being in contact with the biopharmaceutical substance).

The term "outer" refers to what faces towards the outside or is situated further towards the outside, while the term "inner" relates to what faces towards the inside or is situated further towards the inside. The terms "outer" and "inner" should thus be considered to be relative terms.

The walls 6 of such biopharmaceutical bags 2 are suitable for: providing a barrier having a high degree of impermeability to gas; being capable of mechanically containing the biopharmaceutical substance situated in the bag 2; being capable of avoiding undesirable interactions with the environment or with the biopharmaceutical substance; being clean, in particular with regard to particles or biologically; being non-degradable, and having high chemical resistance; enabling the biopharmaceutical substance to be produced, preserved, stored, transported, and used safely; being suitable for being fused; being easily folded and unfolded or inflated and deflated without being damaged; and having qualities as regards, in particular, adherence, flexibility, opacity or, conversely, transparence, these characteristics being in no way exclusive of other characteristics.

The material forming the inside face 6b of such a biopharmaceutical bag 2 is, in the embodiment in question, chosen from the family comprising polyethylene (PE) and in particular linear low-density polyethylene (LLDPE), polyethylene vinyl acetate (EVA), polypropylene (PP), ethylenetetrafluoroethylene (ETFE), polyvinylidene fluoride (PVDF), and equivalent materials, in the context of the purpose and application in question. Under no circumstances is the material forming the inside face 6b, polyvinyl chloride (PVC).

In the assembled biopharmaceutical device 1, the end portion 5a of the segment of biopharmaceutical tube 5 is associated in communicating, continuous, rigid, and leaktight manner, by fusing, with the access 3 via the biopharmaceutical connector 4, which is itself associated in communicating, continuous, rigid, and leaktight manner, by fusing, with the wall 6 of the bag 2 at the access 3.

In an embodiment given merely by way of non-limiting example, the biopharmaceutical connector 4 that is provided with a central axis, has, in one piece, a hollow segment 7 that is of generally cylindrical shape or of pseudo-cylindrical shape, open at both ends 8a and 8b, and a transverse flange 9, extending outwards, i.e. away from the axis of the connector 4.

The transverse flange 9 is fused to the wall 6 of the biopharmaceutical bag 2, around the hole provided through the wall 6 and forming the access 3. The hollow segment 7 is fused to the end portion 5a of the biopharmaceutical segment of tube 5, these elements being engaged one in the other, e.g. the end portion 5a of the biopharmaceutical tube 5 being placed around and outside the hollow segment 7.

In an embodiment given merely by way of non-limiting example, the peripheral side wall of the biopharmaceutical connector 4 has physico-chemical characteristics identical to or at least functionally analogous to the physico-chemical characteristics of the walls 6 of the biopharmaceutical bag 2.

The biopharmaceutical device 1 may be associated functionally and structurally with one or more flow-stop devices for stopping the biopharmaceutical substance (not shown) from flowing, such as a—removable or non-removable—clamp, coming to close the flexible portion of the biopharmaceutical device 1 at the place at which it is located, by flattening said portion, and more especially the segment of tube 5 or other emptying system at the bottom of the bag.

The biopharmaceutical device 1 may also optionally be associated functionally and structurally with one or more biopharmaceutical systems for mixing or aeration that are not shown (which systems may be said to be "functional biopharmaceutical systems").

The tube 5 in question, which may also be referred to as a "duct", a "conduit", or a "pipe", is a hollow vessel, elongate and of a certain finite length, of generally cylindrical shape or of generally pseudo-cylindrical shape, open at one end or at both ends, and suitable for being filled with biopharmaceutical substance for moving it (e.g. for transferring it to or from a biopharmaceutical bag 2 or between two bags 2) or for allowing it to stand (e.g. to constitute a sample of pharmaceutical substance).

The tube 5 is especially suitable for use in the biopharmaceutical device 1, which excludes use in a catheter or an analogous device or a tube for extracorporeal circulation of blood or for passing fluid during a dialysis, a perfusion, or artificial feeding, or for an analogous purpose and an analogous application, lying within some other technical field.

The term "tube" as used herein applies both when the tube is of long length, as results from its manufacturing process, and also when the tube is of smaller length, such as when it has the length of a segment resulting from cutting a long length and designed to be incorporated into the biopharmaceutical device 1.

The tube 5 has a peripheral side wall 10 and delimits a longitudinal empty space 11 for transferring the biopharmaceutical substance or for allowing it to stand. In another embodiment (not shown), the tube 5 has a plurality of parallel longitudinal empty spaces, separated by one or more walls. It is this longitudinal empty space 11 that may be closed by the biopharmaceutical tube 5 being flattened by a clamp for stopping the biopharmaceutical substance from flowing.

In an embodiment given merely by way of non-limiting example, the tube 5 can be cut up by means of an appropriate cutting tool. It can also be closed off, either by a flow-stop device such as a clamp, as indicated above, or by being fused or by being folded back on itself.

In non-limiting examples, such a biopharmaceutical device 1 constitutes an assembly that may be referred to as a bag for storing and/or filling and/or handling and/or transporting and/or mixing a biopharmaceutical substance or a bioreactor for a biopharmaceutical substance.

More generally, the biopharmaceutical device 1 of the invention may comprise a plurality of biopharmaceutical bags 2, a plurality of accesses 3, a plurality of segments of biopharmaceutical tubes 5 (it being possible, optionally, for two or more segments of biopharmaceutical tubes to be associated with each other functionally and structurally, end-to-end or with branches), optionally a plurality of biopharmaceutical connectors 4, a plurality of stop-flow devices for stopping the biopharmaceutical substance from flowing, optionally one or more mixing and/or aeration biopharmaceutical systems, and more generally functional biopharmaceutical systems, arranged in a configuration adapted to the purpose and to the application for which the biopharmaceutical device 1 is designed.

It is understood that although the biopharmaceutical device 1 taken overall is designed for producing, storing, and transporting a biopharmaceutical substance, and although any component element 2, 4, 5 of the biopharmaceutical device 1 is designed and suitable for receiving the biopharmaceutical substance, the invention also includes the situation when any such component element 2, 4, 5 of the biopharmaceutical device 1 is designed and suitable for receiving one or more components of the biopharmaceutical substance or the biopharmaceutical substance in one or more distinct states. Therefore, it should be understood, in particular, that the biopharmaceutical tube 5 is designed for transferring the biopharmaceutical substance or for allowing it to stand via the longitudinal empty space 11, or that its inside face defining the longitudinal empty space is suitable for being in contact with the biopharmaceutical substance. The invention covers all of these embodiments.

The biopharmaceutical tube 5 is multi-layer, its peripheral side wall 10 having a contact inner layer 12 and a functional outer layer 13 including at least one functional elementary layer 13i. In an embodiment, the multilayer biopharmaceutical tube 5 is made up of the contact layer 12 and of the functional layer 13.

The contact layer 12 constitutes the inside face 14a of the multilayer biopharmaceutical tube 5 that defines the longitudinal empty space 11 and is suitable for being in contact with the biopharmaceutical substance. It is made of a material chosen to be suitable for being in contact with the biopharmaceutical substance without resulting in degradation of the contact layer or of the biopharmaceutical substance, and for being fused to itself, i.e. suitable for performing the containing and physical separation function inherent to a tube.

The material of which the contact layer 12 is made is chosen from the family comprising polyethylene (PE) and in particular linear low-density polyethylene (LLDPE), polyethylene vinyl acetate (EVA), polypropylene (PP), ethylenetetrafluoroethylene (ETFE), and polyvinylidene fluoride (PVDF). Under no circumstances is the material of which the contact layer 12 is made PVC.

The functional layer 13 including at least one functional elementary layer 13i is made of a material chosen, on the basis of the needs of the function and of the purpose of the biopharmaceutical device 1, for its flexibility, robustness, handling, opacity or, conversely, transparence, of being a barrier to gases that is non-degradable intrinsically or in association with a protective layer, i.e. suitable for performing functions making it possible to satisfy the other physical, chemical, biological, and operational properties appropriate for the relevant purpose and application of the multilayer biopharmaceutical tube 5 and, more generally, of the single-use biopharmaceutical device 1.

The material of which a functional elementary layer 13$i$ is made is a material other than PVC and is chosen from the family comprising polyethylene (PE) and in particular linear low-density polyethylene (LLDPE) or polyethylene terephthalate (PET), a polyamide (PA), polyethylene vinyl acetate (EVA), ethylene vinyl alcohol (EVOH), styrene ethylene butadiene styrene (SEBS), polyethylene terephthalate glycol (PETG), and polyvinylidene fluoride (PVDF), in the context of the purpose and of the application in question.

When the multilayer biopharmaceutical tube 5 is made up of the contact layer 12 and of the functional layer 13, the functional layer 13 forms the outside face 14$b$ of the tube 5.

The outer face 15$a$ of the contact layer 12 and the inner face 15$b$ of the functional layer 13 are secured together, the two layers 12 and 13 thus being superposed. Similarly, the outer face and the inner face of two elementary functional layers 13$i$ are secured together.

The term "superposed" as applied to two layers (or optionally to two aggregations of layers), and the term "superposition" should be understood as meaning that the layers (or aggregations of layers) are disposed one on the other directly or, optionally, via a bonding interface layer, without there being any restriction on which layer (or aggregation of layers) is situated above or below the other one, the three-dimensional space of the set formed by these two layers being, a priori, arbitrary.

The term "secured together" as applied to two layers (or aggregations of layers) should be understood as meaning that the two layers (or aggregations of layers) form a coherent assembly, either directly, or, if it is not possible for the two layers (or aggregations of layers) to be secured together directly, because of the materials of which they are respectively made, via a bonding and association interface layer. The person skilled in the art knows what materials can be secured together directly, and what materials require a bonding and association interface layer, and what material to use for making such an interface layer. For reasons of simplification of the description, the description does not indicate whether such a bonding and association interface layer exists, even if such a layer is necessary and designed to be used, the presence of such an appropriate bonding and association interface layer then being implicit for and within the ability of the person skilled in the art.

Superposing the contact layer 12 and the functional layer 13 that make up the wall 10 of the multilayer biopharmaceutical tube 5 makes it possible for said biopharmaceutical tube to satisfy the requirements expected as regards firstly the tube 5 and secondly, more generally, the single-use biopharmaceutical device 1.

The wall 10 of a biopharmaceutical tube 5 that is specially designed and adapted for a single-use biopharmaceutical device 1 must be chosen and designed, in particular as regards its component materials, its shapes, its dimensions, etc., to have a certain amount of flexibility, to be made of plastic, and to be suitable firstly for having the property of containing the contents of the tube and of physically separating the contents from the outside of the tube, and secondly of having physical, chemical, biological, and operational properties adapted to the purpose and to the application in question. Non-limiting examples of such physical, chemical, biological, and operational properties are: providing a barrier having a high degree of impermeability to gas; being capable of mechanically containing the biopharmaceutical substance that is inside the tube 5; capacity of avoiding undesirable interactions with the environment or with the biopharmaceutical substance, e.g. during manufacturing, transport, or storage; capacity of being clean, in particular with regard to particles or biologically; capacity of being non-degradable, and having high chemical resistance; enabling the biopharmaceutical substance to be produced pr preserved safely; being suitable for being fused; being easily folded and unfolded without being damaged; and having qualities as regards, in particular, adherence or flexibility. Depending on the situations, having a certain amount of transparency or, conversely, a certain amount of opacity.

Superposing the contact layer 12 and the functional layer 13 that make up the wall 10 of the multilayer biopharmaceutical tube 5 makes it possible for said biopharmaceutical tube to satisfy the requirements expected, as regards firstly the tube 5 and secondly, more generally, the single-use biopharmaceutical device 1.

The adjective "functional" given to the layer 13 or to the elementary layer 13$i$ does not, however, mean that the contact layer 12 does not have any function. The adjective "contact" given to the contact layer 12 and the adjective "functional" given to the layer 13 mean that the layer 12 essentially performs the function of containing the biopharmaceutical substance (or some component of said biopharmaceutical substance or the biopharmaceutical substance in a particular state) and of physically separating it from the outside of the tube, whereas the layer 13 performs, overall, the functions making it possible to satisfy other physical, chemical, biological, and operational properties adapted to the purpose and to the application in question, the—or each—elementary layer 13$i$ performing one or more of the functions making it possible to satisfy the other physical, chemical, biological, or operational properties required. The contact layer 12 thus does indeed also perform a certain function.

Whereas, by nature, the function of containing and of physically separating is still performed regardless of the multilayer biopharmaceutical tube 5 in question, the functions making it possible to satisfy the other physical, chemical, biological, and operational properties adapted to the purpose and to the application in question can vary quite widely depending on such purposes and applications.

It is possible to consider having a contact layer that, as regards its component materials, has a certain amount of constancy or permanence in the variety of the purposes and applications considered for the multilayer biopharmaceutical tube 5 and the single-use biopharmaceutical device 1. For the functional layer 13, or the—or each—elementary layer 13$i$, it is possible to consider a variety of component materials depending on the physical, chemical, biological, or operational properties required.

The choice of the component materials of the contact layer 12 and of the functional layer 13 lies within the ability of the person skilled in the art, depending on the functions that are to be performed.

The two layers 12 and 13 are secured together by the method of manufacturing the multilayer biopharmaceutical tube 5 (co-extrusion, embedding, cladding, etc.).

The contact layer 12 and the functional layer 13 are chosen, in particular as regards their shapes, and their dimensions, etc. so as to be suitable for performing the functions of containing and of physically separating, and of imparting to the multilayer biopharmaceutical tube 5 physical, chemical, biological, and operational properties adapted to the purpose and to the application in question. These choices are within the ability of the person skilled in the art.

A method of manufacturing such a multilayer biopharmaceutical tube 5 is such that it consists in making available the chosen material suitable for constituting the contact layer 12, the at least one material suitable for constituting the at least one functional elementary layer 13i, and operational fabricability means suitable for making a multilayer tube, and in implementing said fabricability means with the chosen material suitable for constituting the contact layer 12 and the at least one material suitable for constituting the at least one functional elementary layer 13i, so that the outer face 15a of the contact layer 12 and the inner face 15b of the functional layer 13 are secured together.

In a first implementation given by way of example, the method of manufacturing the multilayer biopharmaceutical tube 5 operates continuously, in one or more steps, the multilayer nature being achieved in particular by co-extrusion or embedding.

In a second implementation given by way of example, the manufacturing method operates discontinuously, acting on a segment of tube each time, the multilayer nature being achieved in particular by cladding a segment of tube constituted by the contact layer 12 in an open segment of a tube or of portions of tube(s) that is constituted by the functional layer 13 or a functional elementary layer 13i.

In a manner analogous to the multilayer biopharmaceutical tube(s) 5, the biopharmaceutical bag 2 and, where applicable, a biopharmaceutical connector 4 has/have a contact layer 16 made of a material chosen to be suitable for being in contact with the biopharmaceutical substance without degrading the contact layer or the biopharmaceutical substance and for being fused to itself.

The material of the contact layer 16 of the biopharmaceutical bag 2 and, where applicable, of the biopharmaceutical connector 4 is chosen to be identical or analogous to the material of the contact layer 12 of the multilayer biopharmaceutical tube 5.

The contact layer 16 constitutes the inside face of the biopharmaceutical bag 2 and, optionally, of the biopharmaceutical connector 4, and it is suitable for performing the containing and physical separation function that is inherent to such a bag 2 and to such a connector 4.

The material of the contact layer 16 is chosen from the family comprising polyethylene (PE) and in particular linear low-density polyethylene (LLDPE), polyethylene vinyl acetate (EVA), polypropylene (PP), ethylene-tetrafluoroethylene (ETFE), polyvinylidene fluoride (PVDF), and equivalent materials, in the context of the purpose and application in question. Under no circumstances is the material forming the contact layer 16 PVC.

In an implementation that is given by way of non-limiting example, the biopharmaceutical bag 2 and, optionally, a biopharmaceutical connector 4 is/are multilayer and of multilayer structure identical or analogous to the multilayer structure of the biopharmaceutical tube(s) 5. In this situation, in addition to the contact layer 16, the biopharmaceutical bag 2, and optionally a biopharmaceutical connector 4, has/have at least one functional elementary layer 17i.

The functional layer 17, or the functional elementary layer 17i, is made of a material chosen, on the basis of the needs of the function and of the purpose of the biopharmaceutical device 1, for its flexibility, robustness, handling, opacity or, conversely, transparence, of being a barrier to gases that is non-degradable intrinsically or in association with a protective layer, i.e. suitable for performing functions making it possible to satisfy the other physical, chemical, biological, and operational properties appropriate for the relevant purpose and application of the single-use biopharmaceutical device 1. That material is other than PVC.

In the biopharmaceutical device 1 as assembled, the contact layer 12 of a multilayer biopharmaceutical tube 5 is fused to the contact layer 16 of the biopharmaceutical bag 2, and, optionally, of another segment of biopharmaceutical tube and/or of the biopharmaceutical connector 4, depending on the configurations and purposes and applications, substantially with physical continuity between the respective contact layers 12 and 16.

In an implementation given by way of non-limiting example, when the biopharmaceutical bag 2, and, optionally, a biopharmaceutical connector 4 is/are multilayer, as described, the functional layer 13 of a multilayer biopharmaceutical tube 5 is, in addition, fused to the functional layer 17 of the biopharmaceutical bag 2, and optionally of another segment of biopharmaceutical tube and/or of the biopharmaceutical connector 4, in particular substantially with physical continuity between the respective functional layers 13 and 17.

In order to manufacture a single-use biopharmaceutical device 1 as described, at least one biopharmaceutical bag 2, at least one segment of biopharmaceutical tube 5, and, optionally, at least one biopharmaceutical connector 5 are made available.

Then, these elements are positioned in the configuration of the biopharmaceutical device 1 to be manufactured.

The elements are then fused together in communicating, continuous, rigid, and leaktight manner, so that the contact layer 12 of a biopharmaceutical tube 5 is fused to the contact layer 16 of the biopharmaceutical bag 2, and, optionally, of another segment of biopharmaceutical tube and/or of the biopharmaceutical connector 4, substantially with physical continuity between the respective contact layers 12 and 16, as indicated above.

The object of the invention is not only a single-use biopharmaceutical device 1 designed for producing, storing, and transporting a biopharmaceutical substance, as described, but also a multilayer biopharmaceutical tube 5 specially adapted and designed for such a single-use biopharmaceutical device 1 and having a contact layer 12 and a functional layer 13 including at least one functional elementary layer 13i, which layers are secured together.

Depending on the implementations and embodiments, such a multilayer biopharmaceutical tube 5 may be of circular or oblong inside and/or outside cross-section. It may include a single longitudinal empty space 11 or a plurality of longitudinal empty spaces juxtaposed with leaktight separation. It may be homogeneous from one end to the other of the segment that it forms, or it may, at least one end portion 5a of the segment that it forms, have an uncovered projecting portion constituted by the contact layer 12, in particular in the form of an outwardly extending transverse flange, such a segment of multilayer biopharmaceutical tube 5 then also performing the function of connector for the single-use biopharmaceutical device 1. Such a tube-connector may be associated with a biopharmaceutical bag 1 or, where applicable with another biopharmaceutical tube 5.

FIG. 4A shows an embodiment in which the multilayer biopharmaceutical tube 5 includes a single functional elementary layer 13, 13a, the functional layer 13 then being single-layer. For example, associated with a contact layer 12 of LLDPE, the multilayer biopharmaceutical tube 5 includes a single functional elementary layer 13, 13a of PE.

In other embodiments, the multilayer biopharmaceutical tube 5 comprises a plurality of functional elementary layers 13*i*, 13*j*, etc., each of which is secured to the adjacent layer(s), the functional layer 13 then being multi-layer.

The term "adjacent" as applied to two layers (or aggregations of layers) should be understood as meaning that said two layers (or aggregations of layers) are contiguous, directly or, optionally, via a bonding interface.

FIG. 4B shows an embodiment in which, associated with a contact layer 12 of LLDPE, the wall 10 of the multilayer biopharmaceutical tube 5 includes a functional elementary layer 13*a* of EVOH, a functional elementary layer 13*b* of PA, and a functional elementary layer 13*c* of PET that forms the outside face of the multilayer biopharmaceutical tube. In this example, the functional elementary layer 13*a* of EVOH is secured to the contact layer 12 of LLDPE, whereas the functional elementary layer 13*c* of PET forms the outside face 14*b* of the multilayer biopharmaceutical tube 5.

FIG. 4C shows an embodiment in which, associated with a contact layer 12 of LLDPE, the wall 10 of the multilayer biopharmaceutical tube 5 includes a functional elementary layer 13*a* of EVOH, a functional elementary layer 13*b* of PA, two functional elementary layers 13*c* of LLDPE, and a functional elementary layer 13*d* of a biodegradable material. In this example, the functional elementary layer 13*a* of EVOH is secured to the contact layer 12 of LLDPE, whereas the functional elementary layer 13*d* of biodegradable material forms the outside face 14*b* of the multilayer biopharmaceutical tube 5.

FIG. 4D shows an embodiment in which, associated with a contact layer 12 of LLDPE, the wall 10 of the multilayer biopharmaceutical tube 5 includes a functional elementary layer 13*a* of biodegradable material, two functional elementary layers 13*b* of LLDPE, a functional elementary layer 13*c* of EVOH and a functional elementary layer 13*d* of PA. In this example, the functional elementary layer 13*a* of biodegradable material is secured to the contact layer 12 of LLDPE, whereas the functional elementary layer 13*d* of PA forms the outside face 14*b* of the multilayer biopharmaceutical tube 5.

FIG. 4E shows an embodiment in which, associated with a contact layer 12 of PE, the wall 10 of the multilayer biopharmaceutical tube 5 includes a functional elementary layer 13*a* of EVA, a functional elementary layer 13*b* of EVOH, a functional elementary layer 13*c* of EVA, and a functional elementary layer 13*d* of PE. In this example, the functional elementary layer 13*a* of EVA is secured to the contact layer 12 of PE, whereas the functional elementary layer 13*d* of PE forms the outside face 14*b* of the multilayer biopharmaceutical tube 5.

FIG. 4F shows an embodiment in which, associated with a contact layer 12 of LLDPE, the wall 10 of the multilayer biopharmaceutical tube 5 includes a functional elementary layer 13*a* of EVOH, a functional elementary layer 13*b* of LLDPE, and a functional elementary layer 13*c* of PE. In this example, the functional elementary layer 13*a* of EVOH is secured to the contact layer 12 of PE, whereas the functional elementary layer 13*c* of PE forms the outside face 14*b* of the multilayer biopharmaceutical tube 5.

The invention claimed is:

1. A single-use biopharmaceutical device for producing, storing, and transporting biopharmaceutical substance, comprising:

at least one multilayer segment of biopharmaceutical tube, having a peripheral side wall limiting a longitudinal empty space and including a contact layer and a functional layer with an outer face of the contact layer and an inner face of the functional layer being secured together;

at least one biopharmaceutical bag; and at least one biopharmaceutical connector; each being single-use and having a contact layer made of a material suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:

the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, essentially for performing the containing and physical separation function of the at least one biopharmaceutical tube and forming said inside face thereof;

the functional layer of the biopharmaceutical tube includes at least one functional elementary layer made of a material chosen for flexibility, robustness, handling, opacity transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making possible to satisfy the other physical, chemical, biological, and operational properties adapted to the relevant purpose and application of the single-use biopharmaceutical device;

the contact layer of the bag is made of a material identical or analogous to the material of the contact layer of the at least one biopharmaceutical tube, the contact layer of the biopharmaceutical tube is welded to the biopharmaceutical connector and the bag is welded to the biopharmaceutical connector.

2. The single-use biopharmaceutical device for producing, storing, and transporting biopharmaceutical substance according to claim 1, wherein the biopharmaceutical bag, and optionally another segment of biopharmaceutical tube and/or the biopharmaceutical connector, welded to at least one biopharmaceutical tube, has a multilayer structure identical or analogous to the multilayer structure of the at least one multilayer biopharmaceutical tube, namely comprising a contact layer and a functional layer including at least one functional elementary layer.

3. The single-use biopharmaceutical device for producing, storing, and transporting biopharmaceutical substance according to claim 2, wherein the functional layer of the at least one biopharmaceutical tube is welded to a functional layer of the biopharmaceutical bag, and optionally of the other segment of biopharmaceutical tube and/or of the biopharmaceutical connector.

4. The single-use biopharmaceutical device for producing, storing, and transporting biopharmaceutical substance according to claim 1, wherein the at least one biopharmaceutical tube is welded to an other component element of the biopharmaceutical bag either directly, thereby intrinsically forming the biopharmaceutical connector, or indirectly via the biopharmaceutical connector.

5. The single-use biopharmaceutical device for producing, storing, and transporting biopharmaceutical substance according to claim 1, wherein the device is associated structurally and functionally, removably or non-removably, at least one flow-stop device for the biopharmaceutical substance in the longitudinal empty space of the at least one biopharmaceutical tube having the form of a clamp suitable for closing the portion of the at least one biopharmaceutical tube at which it is located by flattening the at least one biopharmaceutical tube on itself.

6. The single-use biopharmaceutical device for producing, storing, and transporting biopharmaceutical substance according to claim 1, wherein the device is configured for storing and/or filling and/or handling and/or transporting and/or mixing a biopharmaceutical substance or a bioreactor of a biopharmaceutical substance.

7. A method of manufacturing a single-use biopharmaceutical device for producing, storing, and transporting biopharmaceutical substance according to claim 1, disposed of at least one biopharmaceutical bag, at least one segment of biopharmaceutical tube, and at least one biopharmaceutical connector, and positioning these elements in the configuration of the biopharmaceutical device to be manufactured, and welding them together in communicating, continuous, rigid, and leaktight manner, so that the contact layer of the at least one biopharmaceutical tube is welded to the biopharmaceutical connector so as to have access to the functional layer of the biopharmaceutical bag, of another segment of biopharmaceutical tube with substantial physical continuity between the respective contact layers.

8. A single-use biopharmaceutical device for producing, storing, and transporting biopharmaceutical substance, comprising:
   at least one multilayer segment of biopharmaceutical tube, having a peripheral side wall limiting a longitudinal empty space and including a contact layer and a functional layer with an outer face of the contact layer and an inner face of the functional layer being secured together;
   at least one biopharmaceutical bag; and
   at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:
      the contact layer of the biopharmaceutical tube is made of a other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, suitable essentially for performing the containing and physical separation function of the at least one biopharmaceutical tube and forming said inside face thereof;
      the functional layer of the biopharmaceutical tube includes at least one functional elementary layer made of a material chosen for flexibility, robustness, handling, opacity or, conversely, transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making possible to satisfy the other physical, chemical, biological, and operational properties adapted to the relevant purpose and application of the single-use biopharmaceutical device;
      the contact layer of the bag, of another segment of tube and/or of the connector, is made of a material identical or analogous to the material of the contact layer of the at least one biopharmaceutical tube,
      the contact layer of the biopharmaceutical tube is welded to the biopharmaceutical connector, with substantial physical continuity between the respective contact layers,
      and wherein a supplementary layer is covering the inside of contact layers respectively of the tube and of the bag when making the junction between the respective contact layers so as to guarantee the substantial physical continuity between the respective contact layers.

9. A single-use biopharmaceutical device for producing, storing, and transporting biopharmaceutical substance, comprising:
   at least one multilayer segment of biopharmaceutical tube, having a peripheral side wall limiting a longitudinal empty space and including a contact layer and a functional layer with an outer face of the contact layer and an inner face of the functional layer being secured together;
   at least one biopharmaceutical bag; and
   at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:
      the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, essentially for performing the containing and physical separation function of the at least one biopharmaceutical tube and forming said inside face thereof;
      the functional layer of the biopharmaceutical tube includes at least one functional elementary layer made of a material chosen for flexibility, robustness, handling, opacity or, conversely, transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making it possible to satisfy the other physical, chemical, biological, and operational properties adapted to the relevant purpose and application of the single-use biopharmaceutical device;

the contact layer of the bag, of another segment of tube and/or of a connector, is made of a material chosen to be identical or analogous to the material of the contact layer of the at least one biopharmaceutical tube, the contact layer of the biopharmaceutical tube is welded to the connector, with substantial physical continuity between the respective contact layers, and wherein the connector comprises a hollow segment and a transverse flange disposed so that an end portion of said multilayer tube is placed around and outside said hollow segment and so that said transverse flange is placed around a hole provided through a wall forming access to said biopharmaceutical bag.

10. A single-use biopharmaceutical device for producing, storing, and transporting biopharmaceutical substance, comprising:

at least one multilayer segment of biopharmaceutical tube, having a peripheral side wall limiting a longitudinal empty space and including a contact layer and a functional layer with the outer face of the contact layer and the inner face of the functional layer being secured together;

at least one biopharmaceutical bag; and at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, rigid, and leaktight manner, having a certain amount of flexibility, and being made of plastic, wherein:

the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, i.e. being suitable essentially for performing the containing and physical separation function of the at least one biopharmaceutical tube and forming said inside face thereof;

the functional layer of the biopharmaceutical tube includes at least one functional elementary layer made of a material chosen for its flexibility, robustness, handling, opacity or, conversely, transparence, barrier to gases, non-degradable intrinsically or in association with a protective layer, other than PVC and chosen from the consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, i.e. suitable for performing the functions making it possible to satisfy the other physical, chemical, biological, and operational properties adapted to the relevant purpose and application of the single-use biopharmaceutical device;

the contact layer of the bag, of another segment of tube and/or of a connector, is made of a material chosen to be identical or analogous to the material of the contact layer of the at least one biopharmaceutical tube, the contact layer of the biopharmaceutical tube is welded to the biopharmaceutical connector, with substantial physical continuity between the respective contact layers, wherein the biopharmaceutical connector comprises a hollow segment and a transverse flange disposed so that an end portion of said multilayer tube is placed around and outside said hollow segment and so that said transverse flange is placed around a hole provided through a wall forming access to said biopharmaceutical bag, and wherein said biopharmaceutical connector has, in one piece, said hollow segment and said transverse flange.

11. A single-use biopharmaceutical device for producing, storing, and transporting biopharmaceutical substance, comprising:

at least one multilayer segment of biopharmaceutical tube, having a peripheral side wall limiting a longitudinal empty space and including a contact layer and a functional layer with an outer face of the contact layer and an inner face of the functional layer being secured together;

at least one biopharmaceutical bag; and, at least one biopharmaceutical connector; each being single-use and having a contact layer made of a material suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:

the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, essentially for performing the containing and physical separation function of the at least one biopharmaceutical tube and forming said inside face thereof;

the functional layer of the biopharmaceutical tube includes at least one functional elementary layer made of a material chosen for flexibility, robustness, handling, opacity transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making possible to satisfy the other physical, chemical, biological, and operational properties adapted to the relevant purpose and application of the single-use biopharmaceutical device;

the contact layer of the bag, and/or of the biopharmaceutical connector, is made of a material identical or analogous to the material of the contact layer of the at least one biopharmaceutical tube, the contact layer of the biopharmaceutical tube is welded to the biopharmaceutical connector, with substantial physical continuity between the respective contact and functional layers.

12. A single-use biopharmaceutical device for producing, storing, and transporting biopharmaceutical substance, comprising:
at least one multilayer segment of biopharmaceutical tube, having a peripheral side wall limiting a longitudinal empty space and including a contact layer and a functional layer with an outer face of the contact layer and an inner face of the functional layer being secured together;
at least one biopharmaceutical bag; and
at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:
the contact layer of the biopharmaceutical tube is made of a other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, suitable essentially for performing the containing and physical separation function of the at least one biopharmaceutical tube and forming said inside face thereof;
the functional layer of the biopharmaceutical tube includes at least one functional elementary layer made of a material chosen for flexibility, robustness, handling, opacity or, conversely, transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making possible to satisfy the other physical, chemical, biological, and operational properties adapted to the relevant purpose and application of the single-use biopharmaceutical device;
the contact layer of the bag, and/or of the biopharmaceutical connector, is made of a material identical or analogous to the material of the contact layer of the at least one biopharmaceutical tube,
the contact layer of the biopharmaceutical tube is welded to the biopharmaceutical connector, with substantial physical continuity between the respective contact layers,
and wherein a supplementary layer is covering the inside of contact layers respectively of the tube and of the bag when making the junction between the respective contact layers so as to guarantee the substantial physical continuity between the respective contact layers.

13. A single-use biopharmaceutical device for producing, storing, and transporting biopharmaceutical substance, comprising:
at least one multilayer segment of biopharmaceutical tube, having a peripheral side wall limiting a longitudinal empty space and including a contact layer and a functional layer with an outer face of the contact layer and an inner face of the functional layer being secured together;
at least one biopharmaceutical bag; and
at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, and leaktight manner, having flexibility, and being made of plastic, wherein:
the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, essentially for performing the containing and physical separation function of the at least one biopharmaceutical tube and forming said inside face thereof;
the functional layer of the biopharmaceutical tube includes at least one functional elementary layer made of a material chosen for flexibility, robustness, handling, opacity or, conversely, transparence, barrier to gases, non-degradable intrinsically or in association with a protective layer, other than PVC and chosen from the group consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, for performing the functions making it possible to satisfy the other physical, chemical, biological, and operational properties adapted to the relevant purpose and application of the single-use biopharmaceutical device;
the contact layer of the bag, and/or of the biopharmaceutical connector, is made of a material chosen to be identical or analogous to the material of the contact layer of the at least one biopharmaceutical tube,
the contact layer of the biopharmaceutical tube is welded to the biopharmaceutical connector, with substantial physical continuity between the respective contact layers,
and wherein the biopharmaceutical connector comprises a hollow segment and a transverse flange disposed so that an end portion of said multilayer tube is placed around and outside said hollow segment and so that said transverse flange is placed around a hole provided through a wall forming access to said biopharmaceutical bag.

14. A single-use biopharmaceutical device for producing, storing, and transporting biopharmaceutical substance, comprising:
at least one multilayer segment of biopharmaceutical tube, having a peripheral side wall limiting a longitudinal empty space and including a contact layer and a functional layer with the outer face of the contact layer and the inner face of the functional layer being secured together;

at least one biopharmaceutical bag; and at least one biopharmaceutical connector; each being single-use and having a contact layer made of a material chosen to be suitable for being in contact with the biopharmaceutical product without resulting in degradation of the contact layer or of the biopharmaceutical substance, and for being weldable to itself, welded together in communicating, continuous, rigid, and leaktight manner, having a certain amount of flexibility, and being made of plastic, wherein:

the contact layer of the biopharmaceutical tube is made of a material other than PVC, and chosen from the group consisting of polyethylene, linear low-density polyethylene, polyethylene vinyl acetate, polypropylene, ethylene-tetrafluoroethylene, and polyvinylidene fluoride, the inside face limiting the longitudinal empty space and being suitable for being in contact with the biopharmaceutical substance, i.e. being suitable essentially for performing the containing and physical separation function of the at least one biopharmaceutical tube and forming said inside face thereof;

the functional layer of the biopharmaceutical tube includes at least one functional elementary layer made of a material chosen for its flexibility, robustness, handling, opacity or, conversely, transparence, barrier to gases, non-degradable intrinsically or in association with a protective layer, other than PVC and chosen from the consisting of polyethylene, linear low-density polyethylene, polyethylene terephthalate, a polyamide, polyethylene vinyl acetate, ethylene vinyl alcohol, styrene ethylene butadiene styrene, polyethylene terephthalate glycol, and polyvinylidene fluoride, i.e. suitable for performing the functions making it possible to satisfy the other physical, chemical, biological, and operational properties adapted to the relevant purpose and application of the single-use biopharmaceutical device;

the contact layer of the bag, and/or of the biopharmaceutical connector, is made of a material chosen to be identical or analogous to the material of the contact layer of the at least one biopharmaceutical tube, the contact layer of the biopharmaceutical tube is welded to the biopharmaceutical connector, with substantial physical continuity between the respective contact layers, wherein the biopharmaceutical connector comprises a hollow segment and a transverse flange disposed so that an end portion of said multilayer tube is placed around and outside said hollow segment and so that said transverse flange is placed around a hole provided through a wall forming access to said biopharmaceutical bag, and wherein said biopharmaceutical connector has, in one piece, said hollow segment and said transverse flange.

* * * * *